United States Patent
Coe et al.

[11] Patent Number: 5,716,604
[45] Date of Patent: Feb. 10, 1998

[54] CLEAR COSMETIC STICK COMPOSITION WITH 2-METHYL-1,3-PROPANEDIOL

[75] Inventors: Craig M. Coe, Buzzards Bay; Chinyere E. Onyekachi Utaegbulam, Medfield; Yanick Jean, Arlington; Tuan M. Vu, Allston; Jayant N. Sane, Framingham, all of Mass.

[73] Assignee: The Gillette Company, Boston, Mass.

[21] Appl. No.: 713,223

[22] Filed: Sep. 24, 1996

Related U.S. Application Data

[63] Continuation-in-part of Ser. No. 543,535, Oct. 17, 1995, abandoned.

[51] Int. Cl.$^6$ .............................. A61K 7/32; A61K 7/00
[52] U.S. Cl. .................... 424/65; 424/66; 424/67; 424/68; 424/400; 424/401; 424/DIG. 5
[58] Field of Search .................. 424/65, 66, 67, 424/68, 400, 401, DIG. 5

[56] References Cited

U.S. PATENT DOCUMENTS

| | | | |
|---|---|---|---|
| 4,226,889 | 10/1980 | Yuhas | 424/59 |
| 4,268,498 | 5/1981 | Gedeon et al. | 424/59 |
| 4,322,400 | 3/1982 | Yuhas | 424/59 |
| 4,440,742 | 4/1984 | Marschner | 424/65 |
| 4,504,465 | 3/1985 | Sampson et al. | 424/65 |
| 4,617,185 | 10/1986 | DiPietro | 424/65 |
| 4,759,924 | 7/1988 | Luebbe et al. | 424/65 |
| 4,906,454 | 3/1990 | Melanson et al. | 424/65 |
| 5,114,717 | 5/1992 | Kuznitz et al. | 424/65 |
| 5,120,541 | 6/1992 | Macaulay et al. | 424/59 |
| 5,128,123 | 7/1992 | Brewster et al. | 424/65 |
| 5,221,529 | 6/1993 | Tansley | 424/65 |
| 5,368,848 | 11/1994 | Brazinsky et al. | 424/65 |
| 5,407,668 | 4/1995 | Kellner | 424/65 |
| 5,424,070 | 6/1995 | Kasat et al. | 424/65 |
| 5,443,821 | 8/1995 | Smith et al. | 424/65 |
| 5,458,880 | 10/1995 | Kasat et al. | 424/65 |
| 5,462,736 | 10/1995 | Rech et al. | 424/65 |
| 5,585,092 | 12/1996 | Trandai et al. | 424/65 |

FOREIGN PATENT DOCUMENTS

| | | |
|---|---|---|
| 089120 | 9/1983 | European Pat. Off. |
| 284765 | 10/1988 | European Pat. Off. |
| 521579 | 1/1993 | European Pat. Off. |

OTHER PUBLICATIONS

M. de Navarre, The Chemistry and Manufacture of Cosmetics, vol. IV, p. 697 (1975).
MPDiol Glycol, Unique Properties, ARCO Chemical (1994).
Chemical & Engineering News, vol. 74, No. 27 (Jul. 1, 1996), pp. 13 & 18.

*Primary Examiner*—Shelley A. Dodson
*Attorney, Agent, or Firm*—Stephan P. Williams

[57] ABSTRACT

Soap-based clear cosmetic sticks are disclosed which include 2-methyl-1,3-propanediol in the composition to increase the set temperature, and also the stick hardness. A typical composition of the present invention comprises about 20 to 50%, preferably 28 to 46%, of 2-methyl-1,3-propanediol, about 3 to 12%, preferably 4 to 8%, of an alkali metal salt of a $C_{12-22}$, preferably $C_{14-18}$, fatty acid, about 10 to 42%, preferably 18 to 30%, of a polyhydric alcohol other than 2-methyl-1,3-propanediol, and about 5 to 35%, preferably 15 to 30%, water. To achieve the highest set temperature the composition should also contain an alkali metal salt, preferably a sodium or potassium salt, particularly an alkali metal halide such as sodium chloride or an alkali metal chelate such as di-, tri- or tetra-sodium EDTA. The composition will also typically contain a cosmetic active ingredient such as a deodorant active. Preferably the composition will contain less than 0.3%, most preferably less than 0.2%, of $C_{20-22}$ soap in order to achieve maximum clarity.

18 Claims, No Drawings

CLEAR COSMETIC STICK COMPOSITION WITH 2-METHYL-1,3-PROPANEDIOL

BACKGROUND OF THE INVENTION

This application is a continuation-in-part of Ser. No. 08/543,535 filed on Oct. 17, 1995 abandoned Jun. 19, 1997.

The present invention relates to clear cosmetic stick compositions, particularly deodorant stick compositions, of improved clarity and stability.

Clear cosmetics sticks comprising a monohydric and/or polyhydric alcohol, a soap gelling agent, and optionally water and one or more emollients are well-known in the art. U.S. Pat. No. 4,226,889 (Yuhas) describes a deodorant stick composition consisting essentially of an aqueous sodium stearate vehicle (100 parts water and 1 to 30 parts sodium stearate) with 0.05 to 0.5% bacteriostat and 0.5 to 10% polyhydroxyl compound. U.S. Pat. No. 4,322,400 (Yuhas) suggests that the setting point of the foregoing composition can be increased by adding 0.5 to 5% sodium chloride. U.S. Pat. No. 4,268,498 (Gedeon) discloses a clear cosmetic stick containing 2 to 5% polyoxyethylene (17–23)-glucose fatty acid ester, 2 to 5% polyoxyethylene (20–60) ether of a long chain alcohol, 24 to 72% PPG(2–5) ether of a long chain alcohol, 5 to 8% soap, 5 to 10% propylene glycol, 5 to 10% lower alkyl ester of a fatty acid, and 2 to 5% water. U.S. Pat. No. 4,617,185 (DiPietro) discloses a deodorant gel stick comprising 6 to 70% polyhydric alcohol, 3 to 10% soap, and 15 to 40% diisopropyl adipate, optionally with 10 to 60% of a PEG/PPG alcohol condensation product such as PPG-14 butanol.

M. de Navarre, The Chemistry and Manufacture of Cosmetics, vol. IV (1975), p. 697, discloses a clear stick formulation comprising 68% propylene glycol, 7% sodium stearate, 10% water, and 15% Pluronic F-127 ($PEO_{98}$-$PPO_{67}$-$PEO_{98}$). U.S. Pat. No. 4,440,742 Marschner) discloses deodorant sticks comprising 20 to 90% polyhydric alcohol gelled with 2 to 15% soap. Examples 15, 16 and 18 illustrate sticks containing about 44 to 52% propylene glycol or glycerin, 8% sodium stearate, 3 to 4% Procetyl AWS (PPG-5-Ceteth-20), and 35% water. U.S. Pat. No. 4,504,465 (Sampson) discloses a cosmetic gel stick comprising 6 to 70% aliphatic polyhydric alcohol (typically propylene glycol), 3 to 10% soap (typically sodium stearate), and 20 to 80% of a condensation product of the formula $R(OC_3H_6)_a(OC_2H_4)_bOH$ wherein a and b are each 0 to 35 and a+b is 5 to 35 (typically PPG-14 Butanol and PPG-5-Ceteth-20). U.S. Pat. No. 4,759,924 (Luebbe) discloses a clear, cosmetic gel stick containing 40 to 70% aliphatic polyhydric alcohol (typically propylene glycol), 3 to 10% soap (typically sodium stearate), 10 to 40% water, and 1 to 20% of a hydro-alcoholic soluble emollient of the formula $R(OC_3H_6)_a(OC_2H_4)_bOH$ (typically PPG-5-Ceteth-20, PPG-3-Myreth-3, etc.).

U.S. Pat. No. 4,906,454 (Melanson) illustrates in Example 1 a deodorant stick containing 27% propylene glycol, 60% dipropylene glycol, 7% sodium stearate and 4% water. U.S. Pat. No. 5,120,541 (Macaulay) discloses a transparent cosmetic stick which includes 20 to 65% monohydric alcohol, 25.6 to 70% polyhydric alcohol, 3 to 20% soap, 0 to 30% water, and 0.1 to 10% of a soap crystal growth inhibitor such as glycerol monolaurate, sodium ricinoleate, or sodium isostearate.

U.S. Pat. No. 5,128,123 (Brewster) discloses a clear cosmetic stick comprising 10 to 90% polyhydric alcohol, 1 to 40% soap, 1 to 40% alkoxylate copolymer (e.g. Pluronic F-127 or Tetronic 1307), and an amino alcohol clarifying agent (e.g. 2-amino-2-methylpropanol or tetrahydroxypropyl diamine). U.S. Pat. No. 5,221,529 (Tansley) describes a transparent cosmetic stick comprising 20 to 70% glycerol, 3 to 20% soap, 0 to 20% water and 15 to 65% alcohol other than glycerol. U.S. Pat. No. 5,368,848 (Brazinsky) discloses a clear cosmetic stick containing 60 to 90% polyhydric alcohol, 3 to 8% soap, 10 to 20% water, 1 to 7% water soluble emollient having $\geq 20$ PEG groups (e.g. Steareth-100), and 1 to 5% water-dispersible emollient which is a PEG-1 to 6 branched fatty alcohol ether (e.g. Isosteareth-2).

U.S. Pat. No. 5,407,668 (Kellner) discloses a clear deodorant stick comprising 40 to 90% polyhydric alcohol, 10 to 40% water, 1 to 20% soap, 1 to 10% Pentadoxynol-200 and 1 to 20% of a mixture of an alkanolamide (e.g. lauramide DEA) and an alkoxylated alcohol (e.g. Steareth-100 and Isosteareth-2). U.S. Pat. No. 5,424,070 (Kasat) discloses a clear deodorant stick which contains an alkali metal salt of a $C_{12-22}$ fatty acid, with at least some $C_{20-22}$ fatty acid, and a Eumulgin compound, typically PPG-2-Ceteareth-9. Some of the Kasat formulations also include sodium chloride and stearyl alcohol to increase the melting point. U.S. Pat. No. 5,458,880 (Kasat) discloses a clear cosmetic stick comprising an alcohol, water, soap and a sodium salt of a methyl carboxy derivative of ethoxylated lauryl alcohol (e.g. sodium laureth-13 carboxylate).

EP 89,120 (Caserio) discloses a cosmetic gel stick comprising 10 to 50% alkanol (e.g. ethanol), 10 to 50% of a diol chosen from 1,3-, 1,4-, and 2,3-butanediol, 2 to 15% of a soap (e.g. sodium stearate), and 5 to 70% of certain PEG/PPG condensation products (e.g. PPG-14 butyl ether, PPG-5-Ceteth-20). EP 284,765 (Mortillo) discloses gel sticks comprising sodium stearate and 50 to 81% dipropylene glycol, optionally including water, propylene glycol and deodorant active. The stick may also include up to 0.1% sodium metabisulfite or disodium EDTA. EP 521,579 (Moghe) discloses clear cosmetic gel sticks comprising a polyhydric alcohol, water and sodium stearate and further including sodium chloride and stearyl alcohol to reduce crystal formation.

SUMMARY OF THE INVENTION

It has been discovered that in clear cosmetic sticks comprising a polyhydric alcohol and a soap gelling agent, improved clarity and stability can be achieved by incorporating 2-methyl-1,3-propanediol in the composition. In particular, it has been discovered that the inclusion of 2-methyl-1,3-propanediol into the stick composition increases the set temperature, and also the stick hardness, thereby permitting a reduction in the amount of $C_{20-22}$ soap component which would otherwise be required to obtain a sufficiently high set temperature and stick hardness. A typical composition of the present invention comprises about 20 to 50%, preferably 28 to 46%, more preferably 30 to 43%, of 2-methyl-1,3-propanediol, about 3 to 12%, preferably 4 to 8%, of an alkali metal salt of a $C_{12-22}$, preferably $C_{14-18}$, fatty acid, about 10 to 42%, preferably 18 to 30%, of a polyhydric alcohol other than 2-methyl-1,3-propanediol, and about 5 to 35%, preferably 15 to 30%, more preferably 20 to 25%, water. To achieve the highest set temperature the composition should also contain an alkali metal salt, preferably a sodium or potassium salt, particularly an alkali metal halide such as sodium chloride in an amount of about 0.1 to 1%, preferably 0.3 to 0.6%. The composition will also typically contain a cosmetic active ingredient such as a deodorant active. Preferably the composition will contain less than 0.3%, most preferably less than 0.2%, of $C_{20-22}$ soap in order to achieve maximum clarity.

DETAILED DESCRIPTION OF THE INVENTION

The present invention is directed to clear cosmetic stick compositions, particularly clear deodorant stick compositions, comprising 2-methyl-1,3-propanediol, a polyhydric alcohol other than 2-methyl-1,3-propanediol, and a soap gelling agent. A typical composition of the present invention comprises about 20 to 50%, preferably 28 to 46%, more preferably 30 to 43%, of 2-methyl-1,3-propanediol, about 3 to 12%, preferably 4 to 8%, of an alkali metal salt of a $C_{12-22}$, preferably $C_{14-18}$, fatty acid, about 10 to 42%, preferably 18 to 30%, of a polyhydric alcohol other than 2-methyl-1,3-propanediol, and about 5 to 35%, preferably 15 to 30%, more preferably 20 to 25%, water.

The polyhydric alcohol (other than 2-methyl-1,3-propanediol) generally has from 3 to 6 carbon atoms and from 2 to 6 hydroxyl groups and includes, for example, 1,2-propylene glycol, 1,3-propylene glycol, 1,4-butylene glycol, 1,2-butylene glycol, 1,3-butylene glycol, 2,3-butylene glycol, dipropylene glycol, 2,4-dihydroxy-2-methylpentane, glycerin, sorbitol and the like, and mixtures thereof. Most preferred is 1,2-propylene glycol (commonly referred to simply as propylene glycol), which may optionally include one or more of the other aforementioned polyhydric alcohols, preferably dipropylene glycol. An especially preferred cosmetic stick composition will comprise about 15 to about 20% propylene glycol and about 5 to 10% dipropylene glycol. In addition to the polyhydric alcohol, the stick composition may also optionally include up to about 15% of a lower alkanol, such as ethanol, although the inclusion of such material is not preferred.

The soap gelling agent is an alkali metal salt of a $C_{12}$ to $C_{22}$, preferably $C_{14}$ to $C_{18}$, fatty acid. Preferably the soap is sodium stearate, sodium palmitate or a mixture thereof. Commercial grade sodium stearate typically contains other fatty acid components, particularly sodium palmitate. Some commercial grades of sodium stearate also contain significant amounts of $C_{20-22}$ soap, which may be desirable in some products since the presence of higher carbon chain lengths increases the set temperature and hardness of the stick. However, it has been found that such higher carbon chain lengths are not desirable in clear products since they impart some cloudiness. Accordingly, it is preferred that the soap utilized in compositions of the present invention contain less than about 5%, preferably less than about 4%, $C_{20-22}$ (or higher chain length) fatty component so that the final cosmetic stick composition will contain less than 0.3%, most preferably less than 0.2%, of $C_{20-22}$ soap in order to achieve maximum clarity.

It is also preferred to include in the composition an alkali metal salt, preferably a sodium or potassium salt, most preferably a sodium salt, in order to increase the set temperature and hardness of the product to a sufficiently high level. By set temperature is meant the temperature at which a small sample (about 10 ml) of the liquid composition begins to solidify. It is preferred that the compositions of the present invention have a set temperature of at least 44° C., more preferably at least 48° C. The amount of 2-methyl-1,3-propanediol and alkali metal salt should be adjusted so that the final composition has the desired set temperature.

A preferred salt for this purpose is an alkali metal halide, preferably sodium chloride, which can be included in an amount of about 0.1 to 1%, more preferably about 0.3 to 0.6%. Another preferred salt is an alkali metal chelate such as a salt of ethylene diamine tetraacetic acid (EDTA), particularly di-, tri- and tetra-sodium EDTA, with trisodium EDTA being most preferred. These EDTA salts are included in the composition in an amount of about 0.3 to 1.6%, preferably about 0.5 to 1.3%. The EDTA salt serves two purposes—it increases the set temperature and it prevents the formation of precipitates in the composition. Without being bound by any theory, it is believed that the alkali metal portion serves to increase the set temperature in the same manner as the alkali halides described above, while the EDTA portion prevents the formation of precipitates by chelating trace metals that can otherwise form insoluble salts with the soap component. The inclusion of chelating agents for the purpose of preventing precipitate or crystal formation in soap-based clear cosmetic sticks is more fully described in copending application Ser. No. 08/718,884, entitled Clear Cosmetic Stick Composition With Alkali Chelate, filed on Sep. 24, 1996, incorporated herein by reference.

The cosmetic sticks of the present invention may also include various other ingredients provided that they do not adversely affect the clarity of the stick to any significant extent. For example, the stick may include one or more emollients to improve application aesthetics. It may also include a cosmetic active agent such as a deodorant active agent, a perfume or fragrance, cooling agent, skin conditioning agent, sunscreen agent, etc. Particularly preferred is a deodorant active agent which may include bacteriocides, such as triclosan, and malodor-reducing or malodor-masking agents, such as those disclosed in U.S. Pat. No. 5,213,791 (e.g. aminooxyacetic acid) and WO 91/11988. Deodorant actives are typically incorporated in an amount of about 0.1 to 3%.

The cosmetic stick may also optionally include one or more polyethylene oxide and/or polypropylene oxide condensation products, typically in an amount of about 1 to 10%. These include, for example, copolymers of the formula

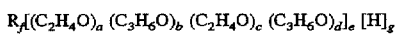

where

R is selected from H, a $C_{12-18}$ fatty alkoxide chain, and ethylene diamine;

a, b, c and d are integers independently selected from 0 to 200, provided that the sum of a, b, c and d is at least 3;

e is an integer from 1 to 4;

f is an integer from 0 to 1; and g is an integer from 0 to 4.

Such copolymers include the Poloxamers (e.g. the Pluronics and Tetronics from BASF Corp.) as well as the PEG and/or PPG fatty alkoxides such as, for example, PPG-3 Myristyl Ether, Isosteareth-20, PPG-5-Ceteth-20, Steareth-100, Oleth-20, and PPG-14 Butyl Ether. Other polyethoxylated derivatives may also be included such as polyoxyethylene ethers of alkyl substituted phenols, e.g. Nonoxynol-4, Nonoxynol-20 and Pentadoxynol-200. Obviously, the copolymer selected should be one which imparts a desirable aesthetic characteristic to the stick without adversely affecting its clarity.

A "clear" stick, as used herein, is a stick that is visually clear so that, like glass, it allows ready viewing of objects behind it. Preferred clear gel sticks have a turbidity measurement, expressed in Nephelometric Turbidity Units (NTU) of less than about 165 NTU, more preferably less than 100 NTU, and most preferably less than 75 NTU, when measured with a Hellige #965 Direct-Reading Turbidimeter.

Preferred cosmetic stick compositions have a hardness of between about 200 and about 400, more preferably between about 225 and about 350, when measured on a TA-XT2 Texture Analyzer (Stable Micro System, Haste Hill, England). These hardness measurements correlate to the grams of force required for the standard arrowhead-type penetration needle to penetrate the stick a distance of 5 mm at 1 mm per second.

The invention may be further illustrated by the following examples in which the parts and percentages are by weight.

EXAMPLES

Deodorant sticks having the compositions shown in the following Table were prepared by combining the ingredients (except fragrance, which is added during cooling) at elevated temperature (typically 80° to 85° C.), pouring into stick-form molds, then cooling under refrigeration at 5° to 15° C. until set. The set temperature for each composition is also given. Each of the sticks was of exceptional clarity.

| Ingredient | Ex. 1 | Ex. 2 | Ex. 3 | Ex. 4 | Ex. 5 | Ex. 6 | Ex. 7 | Ex. 8 | Ex. 9 | Ex. 10 | Ex. 11 | Ex. 12 | Ex. 13 | Ex. 14 |
|---|---|---|---|---|---|---|---|---|---|---|---|---|---|---|
| 2-methyl-1,3-propanediol | 43.1 | 33.2 | 42.2 | 20.0 | 40.0 | 28.2 | 41.5 | 42.0 | 34.7 | 34.7 | 34.7 | 34.7 | 34.7 | 34.7 |
| propylene glycol | 19.6 | 29.6 | 19.6 | 41.7 | 21.1 | 34.6 | 19.6 | 19.6 | 17.2 | 16.1 | 17.5 | 15.4 | 14.5 | 13.2 |
| dipropylene glycol | | | | | | | | | 7.5 | 7.5 | 7.5 | 7.5 | 7.5 | 7.5 |
| water | 19.8 | 19.8 | 19.8 | 19.8 | 21.8 | 19.8 | 21.8 | 19.8 | 21.0 | 23.0 | 23.0 | 23.0 | 25.0 | 25.0 |
| sodium stearate[1] | 5.4 | 5.4 | 5.4 | 5.4 | 5.4 | 5.4 | 5.4 | 5.4 | 5.4 | 5.4 | 5.4 | 5.4 | 5.4 | 5.4 |
| PPG-3 Myristyl Ether | 2.7 | 2.7 | 2.7 | 2.7 | 2.7 | 2.7 | 2.7 | 2.7 | 2.7 | 2.7 | 2.7 | 2.7 | 2.7 | 2.7 |
| Isosteareth-20 | 6.5 | 6.5 | 6.5 | 6.5 | 6.5 | 6.5 | 6.5 | 6.5 | 6.5 | 6.5 | 6.5 | 6.5 | 6.5 | 6.5 |
| diisopropyl sebacate | | 1.0 | 1.0 | 1.0 | | 1.0 | | 1.0 | 1.0 | 1.0 | 1.0 | 1.0 | 1.0 | 1.0 |
| sodium chloride | 0.5 | 0.5 | 0.35 | 0.5 | 0.1 | 0.5 | 0.1 | 0.5 | | | | | | |
| trisodium EDTA | | | | | | | | | | 1.6 | 0.7 | 1.0 | 1.3 | 0.3 | 1.6 |
| triclosan | 0.3 | 0.3 | 0.3 | 0.3 | 0.3 | 0.3 | 0.3 | 0.3 | 0.3 | 0.3 | 0.3 | 0.3 | 0.3 | 0.3 |
| fragrance/preservative | q.s. | q.s. | q.s. | q.s. | q.s. | q.s. | q.s. | q.s. | q.s. | q.s. | q.s. | q.s. | q.s. | q.s. |
| set temperature (°C.) | 49 | 45 | 49 | 42 | 42 | 43 | 44 | 50 | 54 | 50 | 50 | 50 | 50 | 52 |

[1] A blend of 5.0 parts OP-100 and 0.4 parts OP-200 from RTD Chemicals (total $C_{20-22}$ <0.2 parts) except Ex. 8, which is 5.4 parts OP-100 (total $C_{20-22} \cong 0$)

What is claimed is:

1. A clear cosmetic stick composition comprising about 20 to 50% of 2-methyl-1,3-propanediol, about 3 to 12% of an alkali metal salt of a $C_{12-22}$ fatty acid, about 10 to 42% of a polyhydric alcohol other than 2-methyl-1,3-propanediol, and about 5 to 35% water.

2. The composition of claim 1 wherein the polyhydric alcohol has from 3 to 6 carbon atoms and from 2 to 6 hydroxyl groups.

3. The composition of claim 2 having a set temperature of at least 44° C. and a turbidity of less than 100 NTU.

4. The composition of claim 3 having less than 0.3% of $C_{20-22}$ soap component.

5. The composition of claim 1 or 4 wherein the polyhydric alcohol comprises propylene glycol or dipropylene glycol or mixtures thereof.

6. The composition of claim 5 additionally comprising an alkali metal halide or an alkali metal chelate.

7. The composition of claim 6 wherein the alkali metal halide is sodium chloride and the alkali metal chelate is di-, tri- or tetra-sodium EDTA.

8. The composition of claim 7 additionally comprising a deodorant active.

9. The composition of claim 2 comprising about 28 to 46% of 2-methyl-1,3-propanediol, about 4 to 8% of an alkali metal salt of a $C_{14-18}$ fatty acid, about 18 to 30% of a polyhydric alcohol other than 2-methyl-1,3-propanediol, and about 15 to 30% water.

10. The composition of claim 9 having a set temperature of at least 48° C. and a turbidity of less than 100 NTU.

11. The composition of claim 10 having a turbidity of less than 75 NTU.

12. The composition of claim 9 having less than 0.2% of $C_{20-22}$ soap component.

13. The composition of claim 9, 10 or 12 wherein the polyhydric alcohol comprises propylene glycol or dipropylene glycol or mixtures thereof.

14. The composition of claim 13 additionally comprising about 0.1 to 1% of an alkali metal halide or about 0.3 to 1.6% of an alkali metal chelate.

15. The composition of claim 14 wherein the alkali metal halide is sodium chloride and the alkali metal chelate is di-, tri- or tetra-sodium EDTA.

16. The composition of claim 13 additionally comprising about 0.3 to 0.6% of sodium chloride or about 0.5 to 1.3% of di-, tri- or tetra-sodium EDTA.

17. The composition of claim 15 additionally comprising a deodorant active.

18. The composition of claim 17 additionally comprising a copolymer of the formula $$R_f[(C_2H_4O)_a (C_3H_6O)_b (C_2H_4O)_c (C_3H_6O)_d]_e [H]_g$$

where

R is selected from H, a $C_{12-18}$ fatty alkoxide chain, and ethylene diamine;

a, b, c and d are integers independently selected from 0 to 200, provided that the sum of a, b, c and d is at least 3;

e is an integer from 1 to 4;

f is an integer from 0 to 1; and g is an integer from 0 to 4.

* * * * *